(12) United States Patent
Sung et al.

(10) Patent No.: US 11,612,587 B2
(45) Date of Patent: Mar. 28, 2023

(54) COMPOSITION FOR PREVENTING OR TREATING HAIR LOSS

(71) Applicant: KYUNGPOOK NATIONAL UNIVERSITY INDUSTRY-ACADEMIC COOPERATION FOUNDATION, Daegu (KR)

(72) Inventors: Young Kwan Sung, Daegu (KR); Soon Sun Bak, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 16/975,722

(22) PCT Filed: Feb. 19, 2019

(86) PCT No.: PCT/KR2019/001992
§ 371 (c)(1),
(2) Date: Aug. 26, 2020

(87) PCT Pub. No.: WO2019/168290
PCT Pub. Date: Sep. 6, 2019

(65) Prior Publication Data
US 2021/0000793 A1 Jan. 7, 2021

(30) Foreign Application Priority Data
Feb. 28, 2018 (KR) .................. 10-2018-0024508

(51) Int. Cl.
| A61K 31/407 | (2006.01) |
| A23L 29/00 | (2016.01) |
| A61P 17/14 | (2006.01) |
| A61K 8/49 | (2006.01) |
| A61Q 7/00 | (2006.01) |

(52) U.S. Cl.
CPC .......... *A61K 31/407* (2013.01); *A23L 29/045* (2016.08); *A61K 8/492* (2013.01); *A61P 17/14* (2018.01); *A61Q 7/00* (2013.01)

(58) Field of Classification Search
CPC ......... A61Q 7/00; A23L 29/045; A61P 17/14; A61K 31/407; A61K 8/492; A61K 9/0056
See application file for complete search history.

(56) References Cited

U.S. PATENT DOCUMENTS

| 2006/0252812 | A1 | 11/2006 | Chafeev et al. | |
| 2009/0318486 | A1 | 12/2009 | Schwarz et al. | |
| 2011/0112052 | A1 | 5/2011 | Wang et al. | |
| 2012/0289494 | A1 | 11/2012 | Wang et al. | |
| 2016/0192689 | A1* | 7/2016 | Horn | A23L 33/22 424/439 |
| 2016/0346186 | A1* | 12/2016 | Cotsarelis | A61Q 7/00 |

FOREIGN PATENT DOCUMENTS

| CN | 101300259 A | 11/2008 |
| CN | 104602763 A | 5/2015 |
| JP | 2016-106111 A | 6/2016 |
| KR | 10-0682573 B1 | 2/2007 |
| KR | 10-2008-0007581 A | 1/2008 |
| KR | 10-1287052 B1 | 7/2013 |
| KR | 10-1857408 B1 | 5/2018 |
| WO | 01/30151 A1 | 5/2001 |
| WO | 2006-125784 A1 | 11/2006 |
| WO | 2013/142295 A1 | 9/2013 |

OTHER PUBLICATIONS

Crosignani et al., "Discovery of a New Class of Potent, Selective, and Orally Bioavailable CRTH2 (DP2) Receptor Antagonists for the Treatment of Allergic Inflammatory Diseases", 2008, Journal of Medicinal Chemistry, vol. 51, No. 7, pp. 2227-2243. (Year: 2008).*
Joo et al., "15-deoxy prostaglandin J2, the nonenzymatic metabolite of prostaglandin D2, induces apoptosis in keratinocytes of human hair follicles: a possible explanation for prostaglandin D2-mediated inhibition of hair growth", 2016, Naunyn-Schmiedeberg's Arch of Pharmacol, vol. 389, pp. 809-813. (Year: 2016).*
International Search Report for PCT/KR2019/001992 dated May 31, 2019 from Korean Intellectual Property Office.
Crosignani, S. et al., "Discovery of a New Class of Potent, Selective, and Orally Bioavailable CRTH2 (DP2) Receptor Antagonists for the Treatment of Allergic Inflammatory Diseases", Journal of Medicinal Chemistry, 2008, vol. 51, No. 7, pp. 2227-2243.

* cited by examiner

*Primary Examiner* — Michael B. Pallay
(74) *Attorney, Agent, or Firm* — Revolution IP, PLLC

(57) ABSTRACT

The present invention relates to a pharmaceutical composition for preventing or treating hair loss, a health functional food composition or a cosmetic composition, including a specific compound or a pharmaceutically acceptable salt thereof as an active ingredient, wherein the compound exhibits an excellent hair growth recovery effect in hair follicle tissues in which hair growth is inhibited without cytotoxicity, and thus hair loss can be more effectively prevented, improved, or treated.

8 Claims, 6 Drawing Sheets

[FIG. 1]
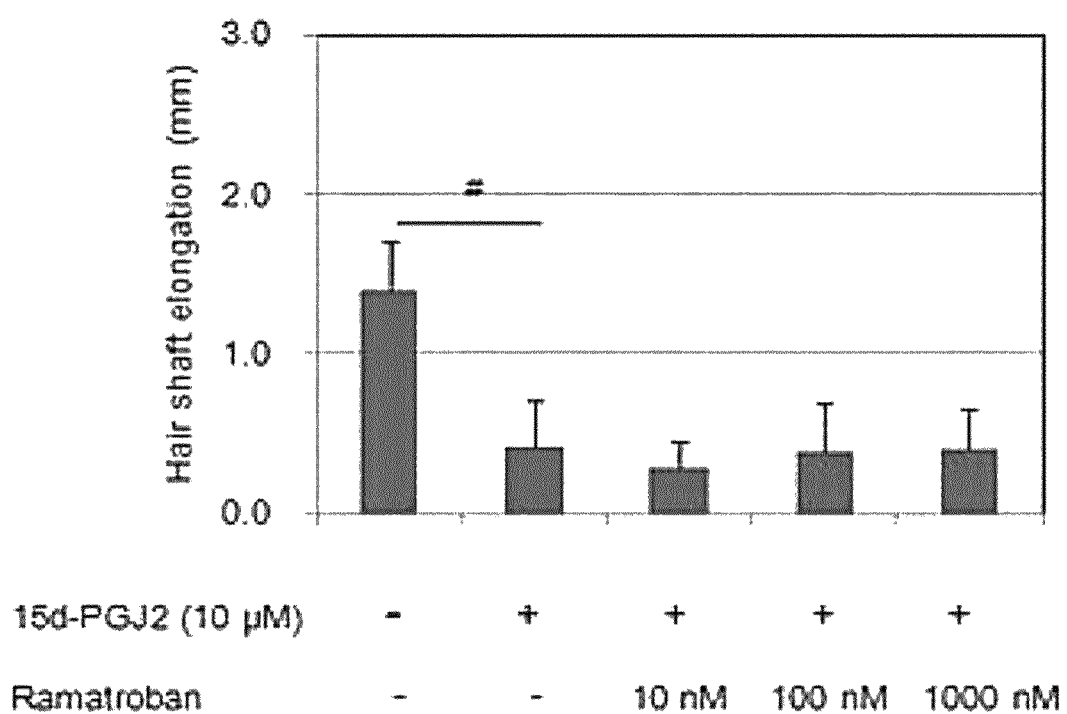

[FIG. 2]
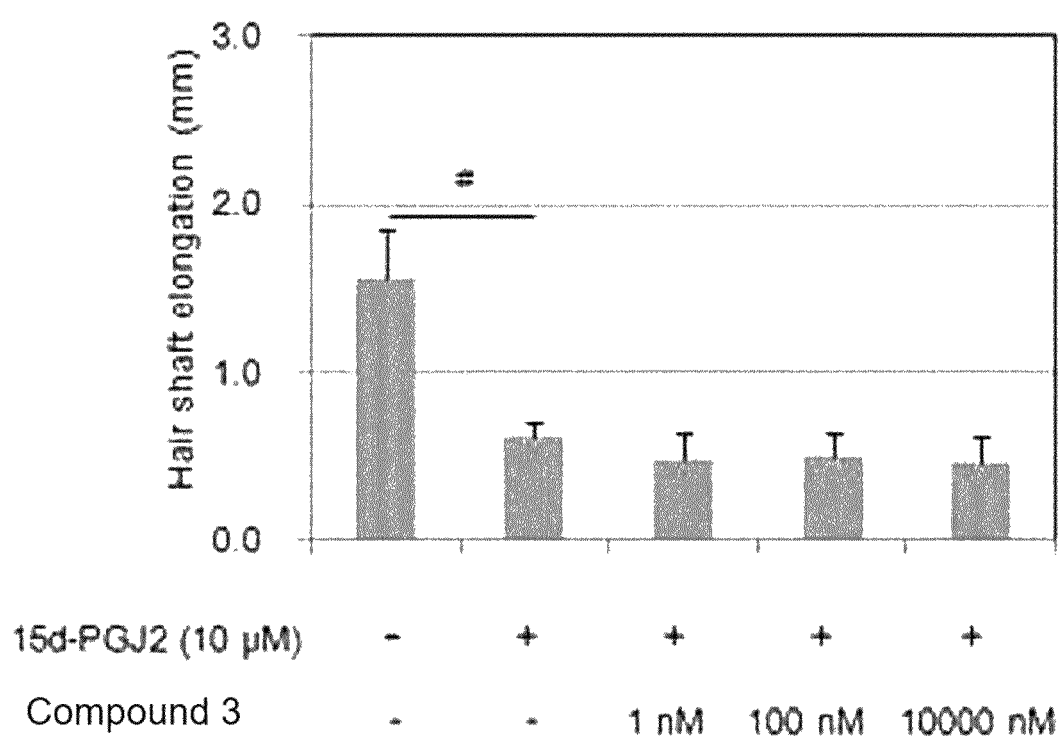

[FIG. 3]
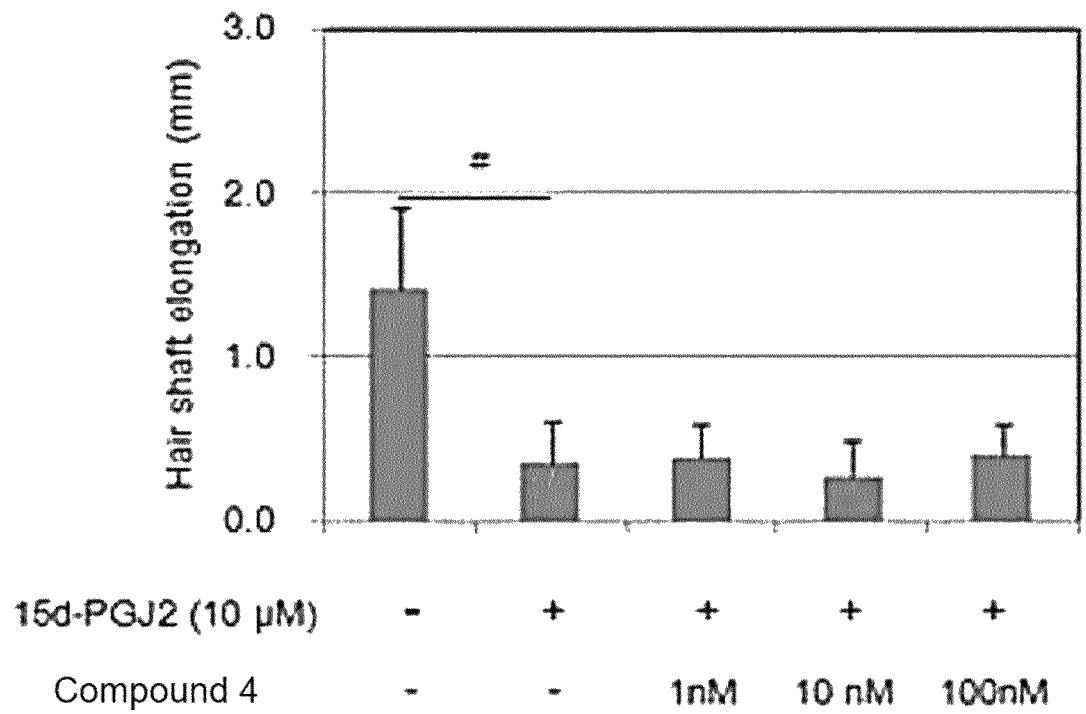
[FIG. 4]
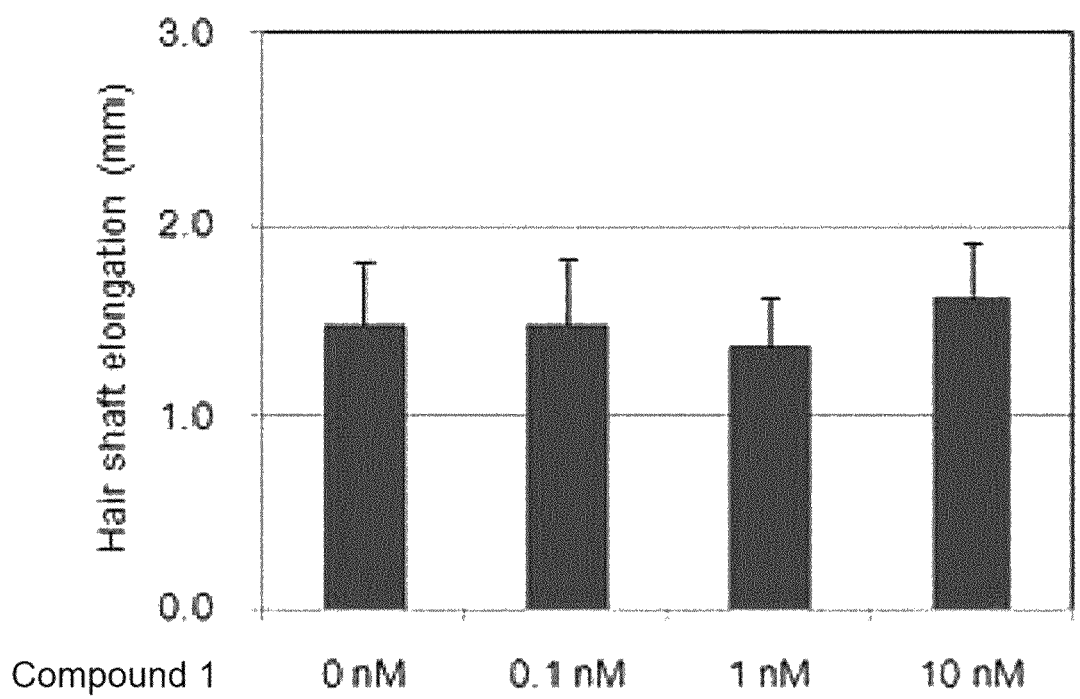

[FIG. 5]
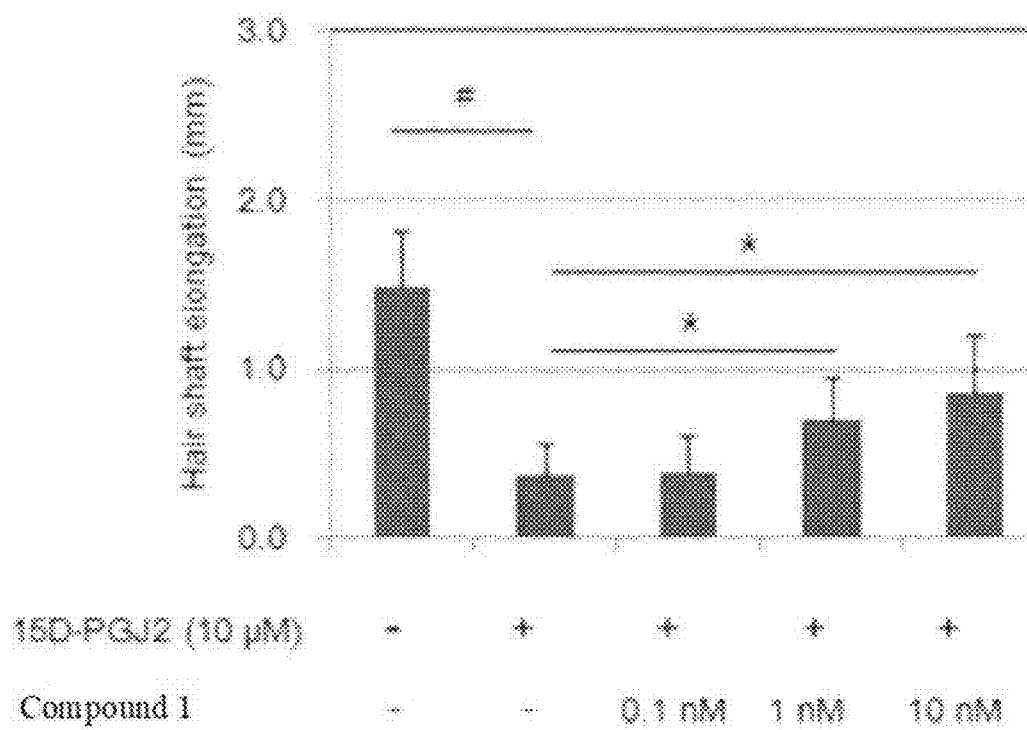

[FIG. 6]
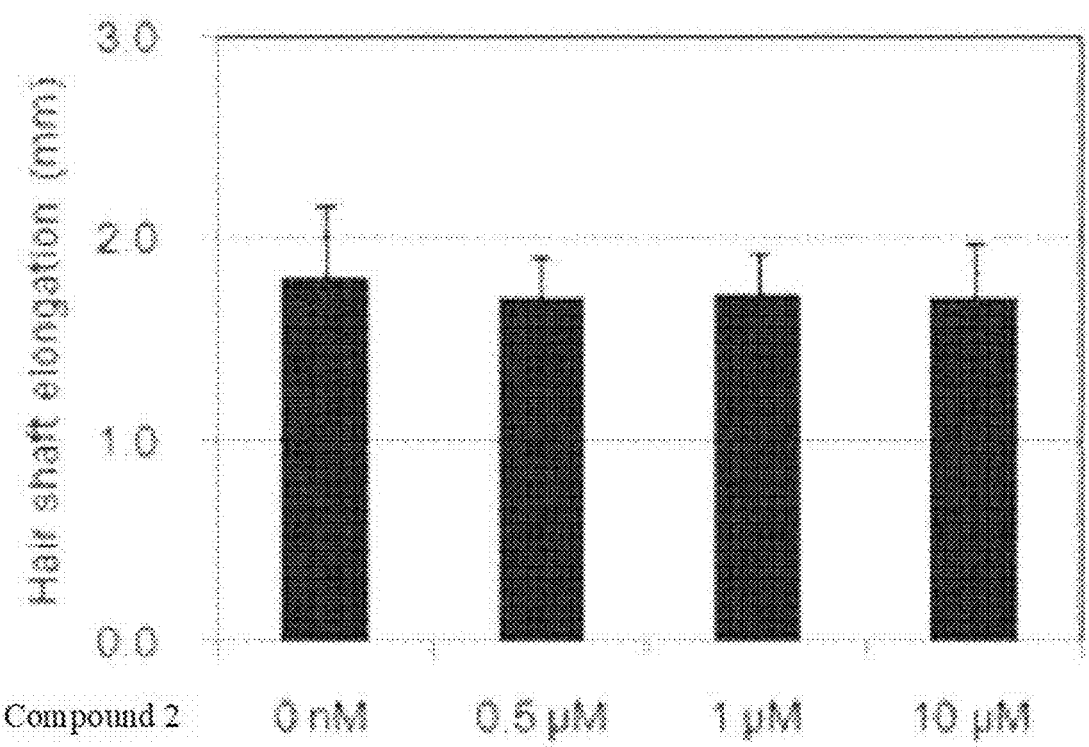

[FIG. 7]
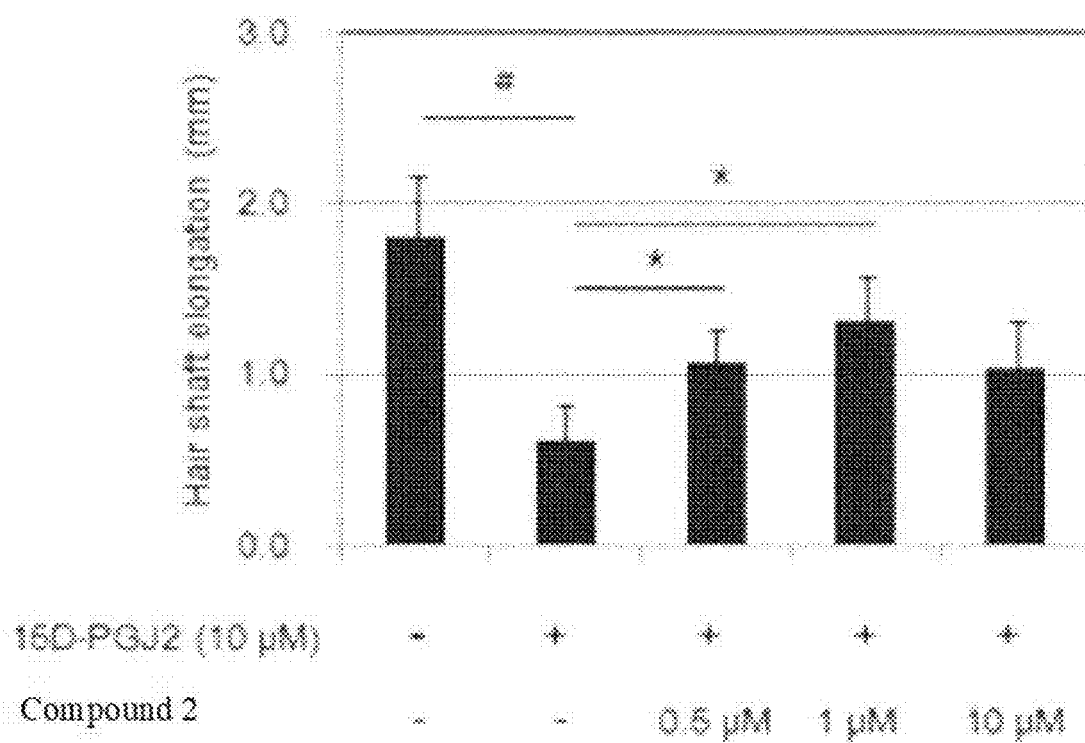

COMPOSITION FOR PREVENTING OR TREATING HAIR LOSS

CROSS REFERENCE TO PRIOR APPLICATIONS

This application is a National Stage Application of PCT International Patent Application No. PCT/KR2019/001992 filed on Feb. 19, 2019, under 35 U.S.C. § 371, which claims priority to Korean Patent Application No. 10-2018-0024508 filed on Feb. 28, 2018, which are all hereby incorporated by reference in their entirety.

TECHNICAL FIELD

The present invention relates to a composition for preventing or treating hair loss comprising a specific compound as an active ingredient.

BACKGROUND ART

Human hair is very important as it plays a unique role in social and sexual communication, as well as its primary role in protecting the skin and scalp. Accordingly, studies on hair and hair loss are continuously in progress, and research and development on a composition for preventing and treating hair loss are going on continuously. Recently, studies on many regulatory factors involved in hair growth and hair loss mechanisms, especially in the hair cycle in the anagen, catagen and telogen have been actively conducted, and it has been continuously reported that they are regulated by signaling by the receptors thereof.

There are many various products related to hair growth currently on the market, but the effect for hair loss prevention and hair growth are mostly inadequate or temporary, so they do not meet the needs of users, and the evidence data on efficacy and safety are insufficient. Minoxidil and Propecia, which are approved by the US FDA and commercially available, are also recognized to some extent for effect, but there has a difficulty that when the use is discontinued, serious side effects such as recurrence of alopecia or sexual dysfunction are reported.

Accordingly, in recent years, many attempts have been made to develop new active ingredients for preventing hair loss and promoting hair growth from natural products with few side effects. Research on oriental medicine approaches through substances capable of mainly activating hair root and promoting blood circulation and various herbal medicines are centered by selecting effective substances through search experiments for natural extracts such as *Batryticatus bombyx* and *Elscholtzia patrini*, Such prior art includes Korean Patent Nos. 682573 and 1287052. However, such a conventional extraction process has the advantage that it is simple and can be easily applied, while the extraction efficiency of the active ingredient is inevitably low.

Therefore, there is a need to develop a new hair loss therapeutic agent capable of overcoming the shortcomings of the composition for treating hair loss comprising such an extract.

DISCLOSURE

Technical Problem

An object of the present invention is to provide a pharmaceutical composition for preventing or treating hair loss comprising a specific compound as an active ingredient.

Another object of the present invention is to provide a health functional food composition for preventing or improving hair loss comprising a specific compound as an active ingredient.

Another object of the present invention is to provide a cosmetic composition for preventing or improving hair loss comprising a specific compound as an active ingredient.

Technical Solution

In order to achieve the above object, the present invention provides a pharmaceutical composition for preventing or treating hair loss comprising a compound represented by the following Chemical Formula 1 or 2, or a pharmaceutically acceptable salt thereof as an active ingredient.

In order to achieve the above other object, the present invention provides a health functional food composition for preventing or improving hair loss comprising a compound represented by the following Chemical Formula 1 or 2, or a pharmaceutically acceptable salt thereof as an active ingredient.

In order to achieve the above another object, it provides a cosmetic composition for preventing or improving hair loss comprising a compound represented by the following Chemical Formula 1 or 2, or a pharmaceutically acceptable salt thereof as an active ingredient.

[Chemical Formula 1]

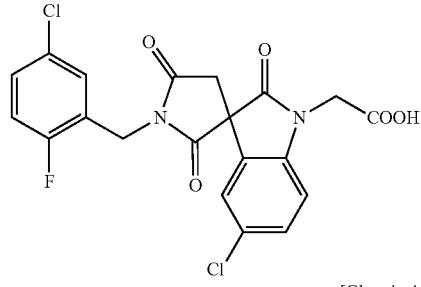

[Chemical Formula 2]

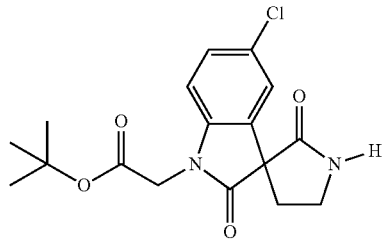

Advantageous Effects

The present invention relates to a composition for preventing or treating hair loss comprising a compound represented by Chemical Formula 1 or 2, or a pharmaceutically acceptable salt thereof as an active ingredient, wherein the compounds are and shows the activity of restoring the hair growth inhibitory effect in the scalp tissue in which hair loss is induced by 15-deoxy-$\Delta^{12,14}$-prostaglandin J2, and also has no cytotoxicity, so it can be usefully used as a composition for effective hair loss prevention or treatment through an excellent hair follicle growth inhibition recovery effect.

DESCRIPTION OF DRAWINGS

FIG. 1 shows a result of evaluating the recovery of human hair follicle growth inhibition by 15d-PGJ2 of ramatroban in human hair follicle tissue (#: p<0.005).

FIG. 2 shows a result of evaluating the recovery of human hair follicle growth inhibition by 15d-PGJ2 of 2-[3-[(4-fluorophenyl)sulfonyl-methylamino]-1,2,3,4-tetrahydrocarbazol-9-yl]acetic acid (Compound 3) in human hair follicle tissue (#: p<0.005).

FIG. 3 shows a result of evaluating the recovery of human hair follicle growth inhibition by 15d-PGJ2 of [5-fluoro-2-methyl-3-(quinolin-2-ylmethyl)indol-1-yl]acetic acid (Compound 4) in human hair follicle tissue (#: p<0.005).

FIG. 4 shows a result of evaluating the toxicity of Compound 1 represented by Chemical Formula 1 of the present invention in human hair follicle tissue.

FIG. 5 shows a result of evaluating the recovery of human hair follicle growth inhibition by 15d-PGJ2 of Compound 1 of the present invention in human hair follicle tissue (#: p<0.005, *: p<0.05).

FIG. 6 shows a result of evaluating the toxicity of Compound 2 represented by Chemical Formula 2 of the present invention in human hair follicle tissue.

FIG. 7 shows a result of evaluating the recovery of human hair follicle growth inhibition by 15d-PGJ2 of Compound 2 of the present invention in human hair follicle tissue (#: p<0.005, *: p<0.05).

BEST MODE

Hereinafter, the present invention will be described in more detail.

The present invention provides a pharmaceutical composition for preventing or treating hair loss comprising a compound represented by the following Chemical Formula 1 or 2, or a pharmaceutically acceptable salt thereof as an active ingredient.

[Chemical Formula 1]

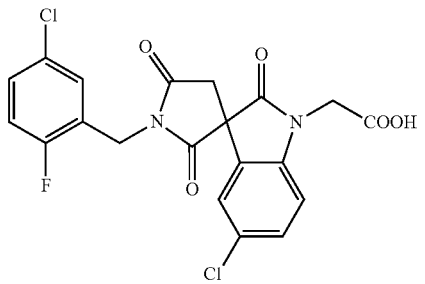

[Chemical Formula 2]

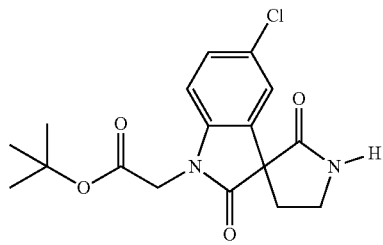

In one embodiment of the present invention, the compounds showed the effect of restoring the growth of hair without cell toxicity in hair follicle tissues in which hair growth is inhibited by 15-deoxy-$\Delta^{12,14}$-prostaglandin J2. Namely, the above compounds can restore the hair growth process inhibited in the hair follicle tissue, and thus can effectively prevent or treat hair loss.

The compound may be included in an amount of 0.0001 to 1 part by weight based on 100 parts by weight of the composition, but it is not limited thereto.

The term "prevention" used in the present invention refers to any action that suppresses or delays disease by administration of composition containing a compound represented by the Chemical Formula 1 (hereinafter referred to as Compound 1) or Chemical Formula 2 (hereinafter referred to as Compound 2), or a pharmaceutically acceptable salt thereof. In addition, the term "treatment" used in the present invention refers to any action in which symptoms of a disease are improved or cured by administration of a composition containing a compound represented by Chemical Formula 1 or 2, or a pharmaceutically acceptable salt thereof.

The compound represented by Chemical Formula 1 or 2 of the present invention may be used in the form of a pharmaceutically acceptable salt, and such salt includes an acid addition salt formed by a pharmaceutically acceptable free acid and a metal salt formed by a base. Inorganic acid and organic acid may be used as the free acid, and the inorganic acid may include hydrochloric acid, sulfuric acid, bromic acid, sulfurous acid or phosphoric acid, etc. The metal salt includes an alkali metal salt or an alkaline earth metal salt, and sodium, potassium or calcium salts are useful.

For administration, the composition of the present invention may include a pharmaceutically acceptable carrier, excipient or diluent in addition to the above-described active ingredients. Examples of the carrier, excipient and diluent include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methylhydroxybenzoate, propyl hydroxybenzoate, talc, magnesium stearate and mineral oils.

The pharmaceutical compositions of the present invention can be formulated and used in the form of oral formulations such as powders, granules, tablets, capsules, suspensions, emulsions, syrups, aerosols, external preparations, suppositories, or sterile injectable solutions according to a conventional method. In detail, when formulated, it may be prepared using diluents or excipients such as fillers, weighting agents, binders, wetting agents, disintegrants and surfactants that are commonly used.

Solid preparations for oral administration include tablets, pills, powders, granules, capsules, and the like, but they are not limited thereto. Such a solid preparation may be prepared by mixing at least one excipient, for example, starch, calcium carbonate, sucrose, lactose, gelatin, etc. to the compound represented by Chemical Formula 1 or 2, or a pharmaceutically acceptable salt thereof. Further, in addition to simple excipients, lubricants such as magnesium stearate and talc may also be used. It can be prepared by adding various excipients such as wetting agents, sweetening agents, fragrances, preservatives, and the like, in addition to liquids and liquid paraffins for oral use.

Formulations for parenteral administration include sterile aqueous solutions, non-aqueous solvents, suspensions, emulsions, lyophilized formulations, and tasks. As the non-aqueous solvent and suspending agent, propylene glycol, polyethylene glycol, vegetable oil such as olive oil, injectable ester such as ethyl oleate, and the like may be used. As a base for suppositories, witepsol, macrosol, Tween 61, cacao butter, laurin, glycerogelatin, and the like may be used.

Formulations for parenteral administration include sterile aqueous solutions, non-aqueous solvents, suspensions, emulsions, freeze drying agents, suppositories. As the non-aqueous solvents and suspensions, propylene glycol, polyethylene glycol, vegetable oils such as olive oil, injectable esters such as ethyl oleate, and the like may be used. As the base of the suppository, witepsol, macrogol, tween 61, cacao butter, laurinum, glycerogelatin and the like may be used.

A suitable dosage of the composition of the present invention varies depending on the condition and weight of the patient, the severity of the disease, the form of the drug, and the time, but can be appropriately selected by a person skilled in the art. Thus, the daily dosage of the pharmaceutically acceptable salt is preferably 1 mg/kg to 500 mg/kg, and may be administered once to several times a day as necessary, but it may be appropriately added or subtracted.

In addition, the present invention provides a health functional food composition for preventing or improving hair loss comprising a compound represented by the following Chemical Formula 1 or 2, or a pharmaceutically acceptable salt thereof as an active ingredient.

[Chemical Formula 1]

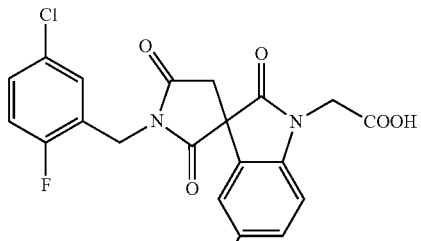

[Chemical Formula 2]

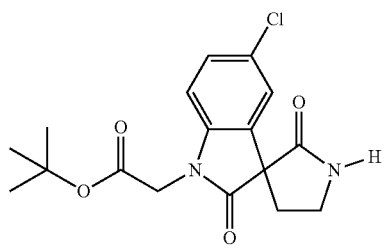

The compounds can restore the hair growth process inhibited in the hair follicle tissue, and can more effectively prevent or improve hair loss.

The compound may be included in an amount of 0.0001 to 1 part by weight based on 100 parts by weight of the composition, but it is not limited thereto.

The health functional food composition may contain various nutrients, vitamins, minerals (electrolytes), flavors such as synthetic flavors and natural flavors, etc., colorants and fillers (cheese, chocolate etc.), pectic acid and its salts, alginic acid and its salts, organic acids, protective colloid thickeners, pH adjusting agents, stabilizers, preservatives, glycerin, alcohols, carbonating agents used in carbonated drinks, and the like. It may also contain flesh for the production of natural fruit juices, synthetic fruit juices and vegetable drinks. These components may be used independently or in combination.

In addition, the health functional food composition may be in the form of any one of meat, sausage, bread, chocolate, candy, snack, confectionery, pizza, ramen, gum, ice cream, soup, beverage, tea, functional water, drink, alcohol and vitamin complex.

In addition, the health functional food composition may further include a food additive and compliance as a food additive is determined by the standards for the applicable item in accordance with General Regulations and General Test Methods of Korean Food Additives Codex approved by the Ministry of Food and Drug Safety, unless otherwise provided.

Examples of the items published in the above-mentioned "Korean Food Additives Codex" include chemical synthetics such as ketones, glycine, potassium citrate, nicotinic acid, and cinnamic acid and the like, natural additives such as persimmon color, licorice extract, crystalline cellulose, kaoliang color and guar gum and the like, mixed preparations such as L-sodiumglutamate preparation, alkaline agents for noodles, preservative formulation and a tar color formulation and the like.

At this time, the content of the compound represented by Chemical Formula 1 or 2 according to the present invention, or a pharmaceutically acceptable salt thereof, added to the food in the process of preparing the health functional food composition can be appropriately added or subtracted as needed, and is preferable. It is preferable to add 0.0001 parts by weight to 1 part by weight to 100 parts by weight of food.

Furthermore, the present invention provides a cosmetic composition for preventing or improving hair loss comprising a compound represented by the following Chemical Formula 1 or 2, or a pharmaceutically acceptable salt thereof as an active ingredient.

[Chemical Formula 1]

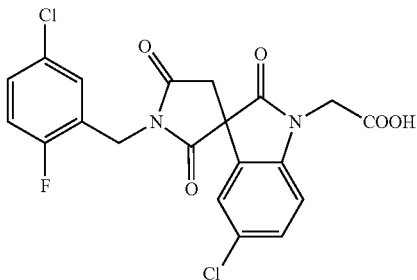

[Chemical Formula 2]

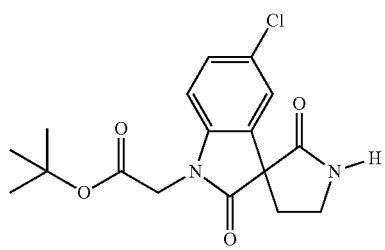

The compounds can restore the hair growth process inhibited in the hair follicle tissue, and can more effectively prevent or improve hair loss.

The compound may be included in an amount of 0.0001 to 1 part by weight based on 100 parts by weight of the composition, but it is not limited thereto.

In one embodiment of the present invention, the cosmetic composition may be any one formulation selected from the group consisting of hair tonic, hair conditioner, hair essence, hair lotion, hair nutrition lotion, hair shampoo, hair conditioner, hair treatment, hair cream, hair nutrition cream, hair moisture cream, hair massage cream, hair wax, hair aerosol, hair pack, hair nutrition pack, hair soap, hair cleansing foam, hair drying preparation, hair preservation treatment, hair dye, hair waving preparation, hair color-removing preparation, hair gel, hair glaze, hair dressinger, hair lacquer, hair moisturizer, hair mousse and hair spray, but it is not limited thereto.

The cosmetic composition of the present invention may include commonly acceptable ingredients in addition to the active ingredients, and may include conventional adjuvants such as antioxidants, stabilizers, solubilizers, vitamins, pigments and fragrances, and a carrier.

When the formulation of the present invention is a paste, cream or gel, animal oil, vegetable oil, wax, paraffin, starch, tragacanth, cellulose derivative, polyethylene glycol, silicone, bentonite, silica, talc, or zinc oxide may be used as carrier components.

When the formulation of the present invention is a powder or spray, lactose, talc, silica, aluminum hydroxide, calcium silicate or polyamide powder may be used as a carrier component, and in particular, in the case of a spray, a propellant such as chlorofluorohydrocarbon, propane/butane or dimethyl ether may be additionally included.

When the formulation of the present invention is a solution or emulsion, a solvent, a solubilizing agent or an emulsifying agent is used as a carrier component, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan.

When the formulation of the present invention is a suspension, liquid diluents such as water, ethanol or propylene glycol, suspending agents such as ethoxylated isostearyl alcohol, polyoxyethylene sorbitol ester and polyoxyethylene sorbitan ester, microcrystalline cellulose, aluminum metahydroxide, bentonite, agar or tragacanth, and the like may be used as carrier components.

In addition, the cosmetic composition of the present invention may be prepared as a hair protection composition including a carrier or a carrier mixture suitable for application to hair. The carrier comprises a carrier component other than a solvent or a vehicle component commonly used in hair protection compositions, and is present from about 0.5% to 99.5%, preferably from about 5.0% to 99.5%, most preferably from about 10.0% to 90.0% of the composition of the total composition. The solvent as a carrier is selected by the copolymer used regardless of whether the formulated hair composition remains on the hair after use, such as hair spray, mousse, tonic, or the like, or is cleaned such as shampoo, conditioner, or the like. Suitable solvents used in the present invention are preferred to include water, lower alcohols (ethanol, isopropanol, etc.), hydroalcohol-based mixtures, hydrocarbons (isobutane, hexane, decene, etc.), acetone, halogenated hydrocarbons (Freon, etc.), hydrocarbon esters (ethyl acetate, dibutyl phthalate, etc.), volatile silicone derivatives, siloxanes (phenyl pentamethyl disiloxane, methoxypropyl heptamethyl cyclotetrasiloxane, chloropropyl pentamethyl disiloxane, hydroxypropyl pentamethyldisiloxane, octamethyl cyclotetrasiloxane, decamethyl cyclopentasiloxane, etc.) and mixtures thereof.

Hereinafter, the present invention will be described in more detail through examples. These examples are only intended to illustrate the present invention in more detail, and it will be apparent to those skilled in the art that the scope of the present invention is not limited by these examples according to the gist of the present invention.

<Example 1> Confirmation of Anti-Hair Loss Effect of Compounds According to the Present Invention First, 15-deoxy-$\Delta^{12,14}$-prostaglandin J2 (15d-PGJ2), a compound which has been approved as a therapeutic agent for allergic rhinitis and is widely used, ramatropan (BAY-u3405), Compound 1 and Compound 2 of the present invention, 2-[3-[(4-fluorophenyl)sulfonyl-methylamino]-1,2,3,4-tetrahydrocarbazol-9-yl]acetic acid (hereinafter referred to as Compound 3) and [5-fluoro-2-Methyl-3-(quinolin-2-ylmethyl)indol-1-yl]acetic acid (hereinafter referred to as Compound 4) were purchased from Cayman chemical (Michigan, USA) and used in the experiment.

Human hair tissue was provided from the hair transplant center of Kyungpook National University and used for the experiment by separating the hair follicles from the scalp tissue with the consent of the hair transplant patient (IRB project number: KNUH2014-02-023). After treatment of each compound, human hair tissue was prepared by incubating a 37° C. $CO_2$ incubator for 6 days using Williams E media (Sigma, USA) containing 2 mM L-glutamine, 100 U/ml streptomycin, and 10 ng/ml hydrocortisone and the length of growth was measured using a microscope.

The data from the above experiments were expressed as mean±SEM. For statistical processing, the mean deviation of each group was measured using Student's t-test, and it was considered significant at $p<0.005$ and $p<0.05$.

As a result, first, as shown in FIG. 1, as a result of treating human hair follicles with 15d-PGJ2 at a concentration of 10 μM, it was found that hair follicle growth decreased by ⅓, which is consistent with the results of the study of Garza et al., (2012) that 15d-PGJ2 inhibited hair follicle growth. The hair follicle growth inhibited by 15d-PGJ2 was not recovered when 15d-PGJ2 and ramatroban (10-1000 nM) were treated simultaneously compared to the treatment with only 15d-PGJ2 (10 μM).

In addition, referring to FIG. 2, when 15d-PGJ2 and Compound 3 (1 to 10000 nM) were simultaneously treated, hair follicle growth inhibited by 15d-PGJ2 was not recovered. Referring to FIG. 3, even when 15d-PGJ2 and Compound 4 (1-100 nM) were simultaneously treated, the hair follicle growth inhibited by 15d-PGJ2 was not recovered.

On the other hand, referring to FIG. 4, when Compound 1 was treated on human hair follicles cultured alone at a concentration of 0.1-10 nM, there was no significant difference from the group not treated with Compound 1. Therefore, it was confirmed that Compound 1 is safe against cultured human hair follicles at the above concentration.

In addition, referring to FIG. 5, when 15D-PGJ2 and Compound 1 were simultaneously treated, the higher the concentration of Compound 1 to 0.1 nM, 1 nM, and 10 nM, it was found that the hair follicle growth inhibited by 15d-PGJ2 significantly increased to 108%, 194%, and 234%, respectively (based on the hair follicle length when 15d-PGJ2 was treated alone as 100%), compared to when only 15d-PGJ2 (10 μM) was treated Meanwhile, referring to FIG. 6, when Compound 2 was treated on human hair follicles cultured alone at a concentration of 0.1 to 10 μM, there was no significant difference from the group not treated with Compound 2. Therefore, it was confirmed that Compound 2 is safe against cultured human hair follicles at the above concentration.

In addition, referring to FIG. 7, when 15D-PGJ2 and Compound 2 were treated at the same time (0.5 μM, 1 μM), hair follicle growth inhibited by 15d-PGJ2 was significantly increased, compared to when only 15d-PGJ2 (10 μM) was treated.

Therefore, the Compounds 1 and 2 according to the present invention are effective in hair follicle growth in the hair loss area where the expression of PGD2 and its metabolite (15d-PGJ2) is high, so it can be usefully used as a composition for preventing or treating hair loss using Compounds 1 and 2 as active ingredients.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of preventing or treating hair loss in a subject in need thereof, comprising:
providing a pharmaceutical composition comprising a compound represented by Chemical Formula 2, or a pharmaceutically acceptable salt thereof as an active ingredient,

[Chemical Formula 2]

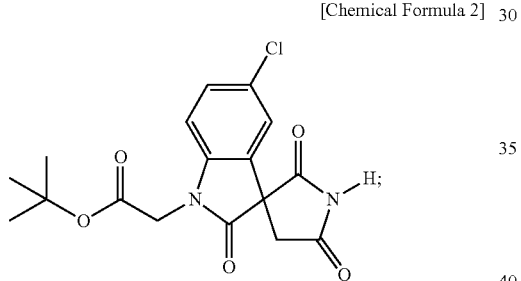

and
administering the pharmaceutical composition to the subject, wherein the hair loss is prevented or treated.

2. The method of claim 1, wherein the compound restores hair growth process inhibited in hair follicle tissue.

3. The method of claim 1, wherein the compound is contained in an amount of 0.0001 to 1 part by weight based on 100 parts by weight of the composition.

4. A method of preventing or improving hair loss in a subject in need thereof, comprising:
providing a health functional food composition comprising a compound represented by Chemical Formula 2, or a pharmaceutically acceptable salt thereof as an active ingredient,

[Chemical Formula 2]

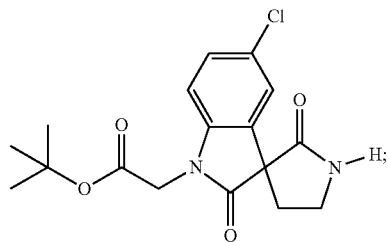

and
administering the health functional food composition to the subject, wherein the hair loss is prevented or improved.

5. The method of claim 4, wherein the compound restores hair growth process inhibited in hair follicle tissue.

6. A method of preventing or improving hair loss in a subject in need thereof, comprising:
providing a cosmetic composition comprising a compound represented by Chemical Formula 2, or a pharmaceutically acceptable salt thereof as an active ingredient,

[Chemical Formula 2]

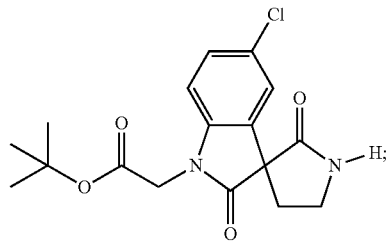

and
applying the cosmetic composition to the subject, wherein the hair loss is prevented or improved.

7. The method of claim 6, wherein the compound restores hair growth process inhibited in hair follicle tissue.

8. The method of claim 6, wherein the cosmetic composition is any one formulation selected from the group consisting of hair tonic, hair conditioner, hair essence, hair lotion, hair nutrition lotion, hair shampoo, hair conditioner, hair treatment, hair cream, hair nutrition cream, hair moisture cream, hair massage cream, hair wax, hair aerosol, hair pack, hair nutrition pack, hair soap, hair cleansing foam, hair drying preparation, hair preservation treatment, hair dye, hair waving preparation, hair color-removing preparation, hair gel, hair glaze, hair dressinger, hair lacquer, hair moisturizer, hair mousse and hair spray.

* * * * *